(12) United States Patent
Lin

(10) Patent No.: US 6,936,716 B1
(45) Date of Patent: Aug. 30, 2005

(54) ORGANOMETALLIC COMPLEX FOR ORGANIC ELECTROLUMINESCENT DEVICE

(75) Inventor: Cheng-Hung Lin, Changhua (TW)

(73) Assignee: Au Optronics Corp., Hsinchu (TW)

( * ) Notice: Subject to any disclaimer, the term of this patent is extended or adjusted under 35 U.S.C. 154(b) by 0 days.

(21) Appl. No.: 10/903,631

(22) Filed: Jul. 30, 2004

(30) Foreign Application Priority Data

May 17, 2004 (TW) ................................. 93113822 A

(51) Int. Cl.$^7$ ........................ C07F 15/00; H05B 33/14; C09K 11/06
(52) U.S. Cl. ...................... 546/2; 548/101; 548/108; 428/432; 428/690; 428/917
(58) Field of Search .............. 546/2; 548/101, 548/108; 428/690, 432

(56) References Cited

U.S. PATENT DOCUMENTS

| | | | |
|---|---|---|---|
| 6,687,266 B1 * | 2/2004 | Ma et al. ........................ 372/7 |
| 2002/0024293 A1 | 2/2002 | Igarashi et al. .............. 313/483 |
| 2002/0182441 A1 | 12/2002 | Lamansky et al. ........... 428/690 |
| 2003/0072964 A1 | 4/2003 | Kwong et al. ............... 428/690 |
| 2003/0116788 A1 | 6/2003 | Sakakibara et al. ......... 257/200 |

FOREIGN PATENT DOCUMENTS

JP 2003109758 * 4/2003

OTHER PUBLICATIONS

Suarez et al., Chemical Abstracts, 103:37584, 1985.*
Suarez et al., Chemical Abstracts, 114:122665, 1991.*

* cited by examiner

Primary Examiner—Fiona T. Powers
(74) Attorney, Agent, or Firm—Thomas, Kayden, Horstemeyer & Risley

(57) ABSTRACT

An organometallic complex having formula (I)

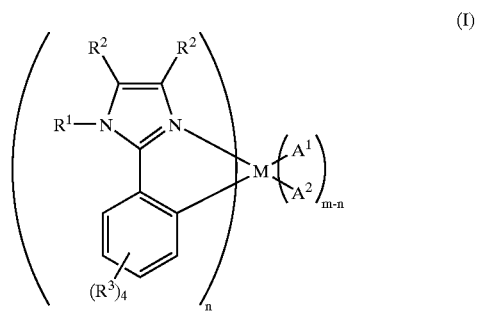

wherein M is a transition metal; each $A^1$ and $A^2$ is independently a monodentate ligand, or $A^1$ and $A^2$ are covalently joined together to form a bidentate ligand; $R^1$ is H, $C_{1-18}$ alkyl, $C_{1-18}$ alkoxy, $C_{3-18}$ heteroalkyl, $C_{3-20}$ aryl, $C_{3-20}$ heteroaryl, or $C_{3-20}$ cycloalkyl; $R^2$ is the same or different and is H, $C_{1-18}$ alkyl, $C_{1-18}$ alkoxy, $C_{3-18}$ heteroalkyl, $C_{3-20}$ aryl, $C_{3-20}$ heteroaryl, or $C_{3-20}$ cycloalkyl, or two $R^2$ groups link together with the carbon atoms to which they are attached to form a 4- to 12-member aromatic or heteroaromatic ring; $R^3$ is the same or different and is H, CN, tricyanovinyl, halogen, $CX_3$, $C_{1-18}$ alkyl, $C_{1-18}$ alkoxy, $C_{3-18}$ heteroalkyl, $C_{3-20}$ aryl, $C_{3-20}$ heteroaryl, or $C_{3-20}$ cycloalkyl, wherein X is halogen; m is the charge of M; n is 1, 2, or 3.

17 Claims, 1 Drawing Sheet

US 6,936,716 B1

ORGANOMETALLIC COMPLEX FOR ORGANIC ELECTROLUMINESCENT DEVICE

BACKGROUND OF THE INVENTION

1. Field of the Invention

The present invention relates to an organometallic complex for an organic electroluminescent device, and more particularly to an organometallic complex serving as a light-emitting layer of an organic electroluminescent device.

2. Description of the Related Art

An organic electroluminescent device (also referred to as organic light-emitting diode; OLED) is an LED with an organic layer serving as the active layer, increasingly applied in flat panel displays due to advantages, such as low voltage operation, high brightness, light weight, slim profile, wide viewing angle, and highly effective contrast ratio.

Generally, an OLED is composed of a light-emitting layer sandwiched by a pair of electrodes. Light emission is caused by the following phenomenon. When an electric field is applied to these two electrodes, the cathode injects electrons into the light-emitting layer and the anode injects holes into the light-emitting layer. When the electrons recombine with the holes in the light-emitting layer and excitons are formed. Recombination of electron and hole is accompanied by emission.

Depending on the spin states of the hole and electron, the exciton which results from hole and electron recombination can have either a triplet or singlet spin state. Luminescence from a singlet exciton results in fluorescence whereas luminescence from a triplet exciton results in phosphorescence. The emissive efficiency of phosphorescence is three times that of fluorescence. Therefore, it is crucial to develop highly efficient phosphorescent material, in order to increase the emissive efficiency of the OLED.

Certain organometallic complexes have been reported as having intense phosphorescence (Lamansky, et al., Inorganic Chemistry, 2001, 40, 1704), and efficient OLEDs emitting in the green to red spectrum have been prepared with these complexes (Lamansky, et al., J. Am. Chem. Soc., 2001, 123, 4304). U.S. Patent Application Publication 2003/0072964A1 discloses a phosphorescent organometallic complex including phenylquinolinato ligands. Other emissive organometallic complexes can be found in U.S. Patent Application Publication 20020024293A1, 20020182441A1 and 20030116788A1.

Relatively good green or red light-emitting organometallic complexes have been developed. More effort in development of organometallic complexes emitting blue light, however, is required.

SUMMARY OF THE INVENTION

An object of the present invention is to provide a novel organometallic complex containing an imidazole ligand.

Another object of the present invention is to provide an organometallic complex having phosphorescence. Electron-withdrawing or electron-donating group can be added on the imidazole ring to change the color of the emitted light. In some embodiments of the present invention, the organometallic complex emits blue light or blue phosphorescence. In some embodiments of the present invention, the organometallic complex of the present invention can have a hole transport property.

Another object of the present invention is to provide an organic electroluminescent device including the organometallic complex of the present invention. The organometallic complex of the present invention can serve as a light-emitting layer in the organic electroluminescent device.

To achieve the above objects, the organometallic complex of the present invention has formula (I)

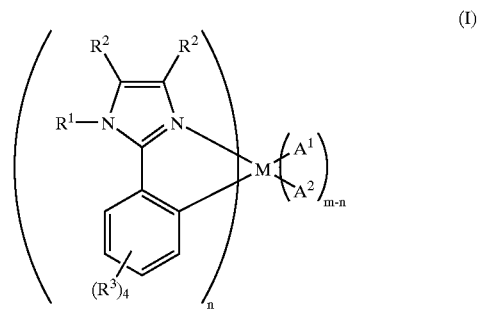

wherein
M is a transition metal;
each $A^1$ and $A^2$ is independently a monodentate ligand, or $A^1$ and $A^2$ are covalently joined together to form a bidentate ligand;
$R^1$ is H, $C_{1-18}$ alkyl, $C_{1-18}$ alkoxy, $C_{3-18}$ heteroalkyl, $C_{3-20}$ aryl, $C_{3-20}$ heteroaryl, or $C_{3-20}$ cycloalkyl;
$R^2$ is the same or different and is H, $C_{1-18}$ alkyl, $C_{1-18}$ alkoxy, $C_{3-18}$ heteroalkyl, $C_{3-20}$ aryl, $C_{3-20}$ heteroaryl, or $C_{3-20}$ cycloalkyl, or two $R^2$ groups link together with the carbon atoms to which they are attached to form a 4- to 14-member aromatic or heteroaromatic ring;
$R^3$ is the same or different and is H, CN, tricyanovinyl, halogen, $CX_3$, $C_{1-18}$ alkyl, $C_{1-18}$ alkoxy, $C_{3-18}$ heteroalkyl, $C_{3-20}$ aryl, $C_{3-20}$ heteroaryl, or $C_{3-20}$ cycloalkyl, wherein X is halogen;
m is the charge of M;
n is 1, 2, or 3.

The organic electroluminescent device of the present invention includes a pair of electrodes and a layer of organic light emitting medium disposed between the pair of electrodes. The layer of organic light emitting medium includes an organometallic complex of formula (I). The layer of organic light emitting medium can include a light emitting layer and a hole transport layer. Either of the light emitting layer or the hole transport layer can include the organometallic complex of formula (I). Or, both the light emitting layer and the hole transport layer can include the organometallic complex of formula (I).

BRIEF DESCRIPTION OF THE DRAWING

The present invention will become more fully understood from the detailed description given hereinbelow and the accompanying drawing, given by way of illustration only and thus not intended to be limitative of the present invention.

DETAILED DESCRIPTION OF THE INVENTION

Figure 1:
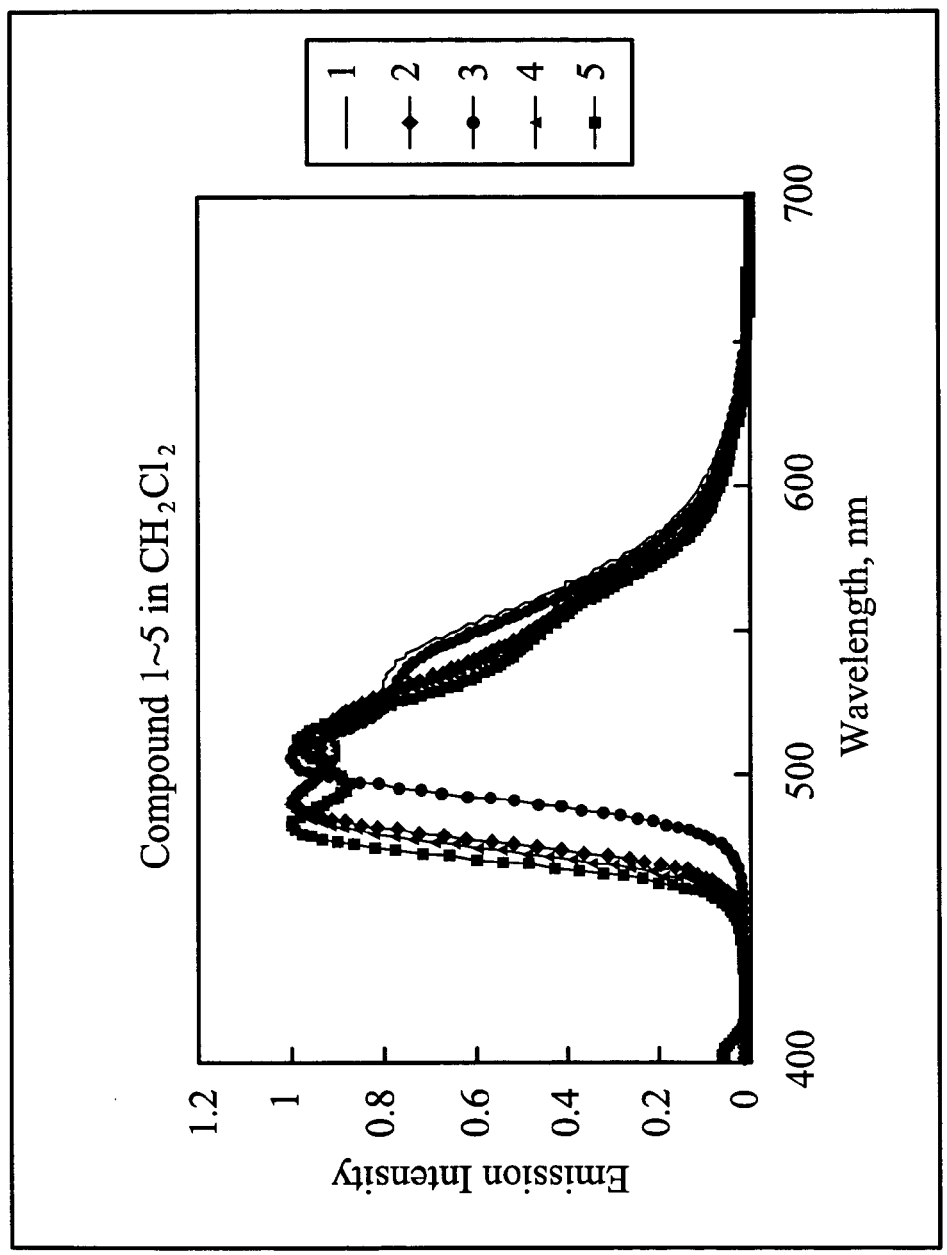
FIG. 1 is a fluorescent spectrum of compounds 1 to of the present invention at various wavelengths.

The present invention provides an organometallic complex containing an imidazole ligand, having formula (I)

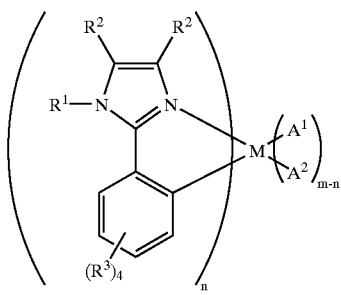

In formula (I), M is a transition metal, preferably having d6 electron orbital. For example, M can be Ir, Pt, Os, Re, Ru, or Rh, preferably Ir.

$A^1$ and $A^2$ can be independently a monodentate ligand. Numerous monodentate ligands are known to those skilled in the art. Representative examples include F, Cl, Br, I, CO, CN, $CN(R^{11})$, $SR^{11}$, SCN, OCN, $P(R^{11})_3$, $P(OR^{11})_3$, $N(R^{11})_3$ NO, and $N_3$, wherein $R^{11}$ is alkyl. In addition, suitable monodentate ligand can be a nitrogen-containing heterocycle, such as pyridine, imidazole, pyrrolidine, piperidine, morpholine, pyrimidine, pyrazine, pyridazine, pyrrole, 1,3,4-triazole, tetrazole, isoxazole, thiazole, derivatives thereof and the like.

Alternatively, $A^1$ and $A^2$ can be covalently joined together to form a bidentate ligand. Numerous bidentate ligands are known to those skilled in the art. Suitable bidentate ligands include acetylacetonate (acac), picolinate (pic), hexafluoroacetylacetonate, salicylidene, 8-hydroxyquinolinate, amino acids, salicylaldehydes, iminoacetonates, biphenyl, bipyridyl, phenylpyridyl, 2-(1-naphthyl)benzoxazole, 2-phenylbenzoxazole, 2-phenylbenzothiazole, coumarin, thienylpyridine, phenylpyridine, benzothienylpyridine, 3-methoxy-2-phenylpyridine, tolylpyridine, phenylimines, vinylpyridines, arylquinolines, pyridylnaphthalenes, pyridylpyrroles, pyridylimidazoles, phenylindoles, derivatives thereof and the like.

$R^1$ is H, $C_{1-18}$ alkyl, $C_{1-18}$ alkoxy, $C_{3-18}$ heteroalkyl, $C_{3-20}$ aryl, $C_{3-20}$ heteroaryl, or $C_{3-20}$ cycloalkyl. Preferably, $R^1$ is an electron-donating group, such as $C_{1-18}$ alkyl, $C_{1-18}$ alkoxy, or $C_{3-18}$ heteroalkyl. Representative examples of electron-donating groups include methyl, methoxy, cyclohexyl. In some embodiments of the present invention, a blue shift of the maximum emission wavelength occurs when $R^1$ is an electron-donating group, e.g., methyl or phenyl.

$R^2$ is the same or different and is H, $C_{1-18}$ alkyl, $C_{1-18}$ alkoxy, $C_{3-18}$ heteroalkyl, $C_{3-20}$ aryl, $C_{3-20}$ heteroaryl, or $C_{3-20}$ cycloalkyl. Preferably, $R^2$ is an electron-donating group, which also induces a blue shift. Representative examples include methyl, tert-butyl, and methoxy. Alternatively, two $R^2$ groups link together with the carbon atoms to which they are attached to form a 4- to 14-member aromatic or heteroaromatic ring. In some embodiments of the present invention, two $R^2$ groups link together with the carbon atoms to which they are attached to form a benzene ring. Other representative examples of 4- to 14-member aromatic ring include naphthalene and phenanthrene.

$R^3$ is the same or different and is H, CN, tricyanovinyl, halogen, $CX_3$, $C_{1-18}$ alkyl, $C_{1-18}$ alkoxy, $C_{3-18}$ heteroalkyl, $C_{3-20}$ aryl, $C_{3-20}$ heteroaryl, or $C_{3-20}$ cycloalkyl, wherein X is halogen. Preferably, $R^3$ is an electron-withdrawing group, such as halogen, CN, tricyanovinyl, or $CX_3$, wherein X is halogen. Suitable electron-withdrawing groups include F, $CF_3$, CN, and tricyanovinyl. In some embodiments of the present invention, a blue shift of the maximum emission wavelength occurs when $R^3$ is an electron-withdrawing group, e.g., F.

The following examples are intended to illustrate the process and the advantages of the present invention without limiting its scope, since numerous modifications and variations will be apparent to those skilled in the art.

EXAMPLES

The following examples prepare compounds 1 to 5, whose chemical structures are shown below.

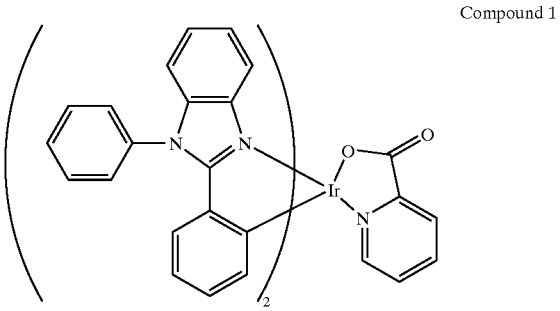

Compound 1

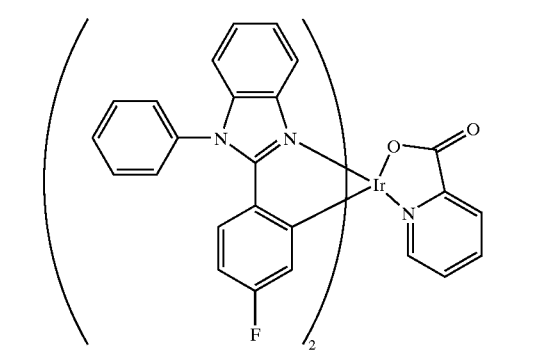

Compound 2

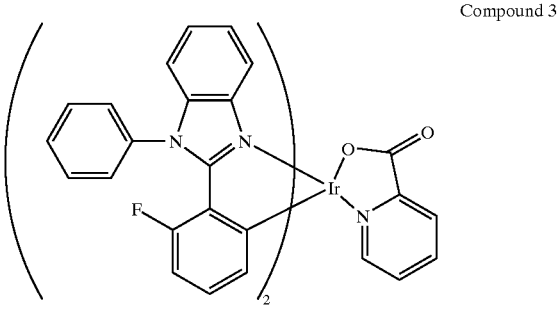

Compound 3

Compound 4

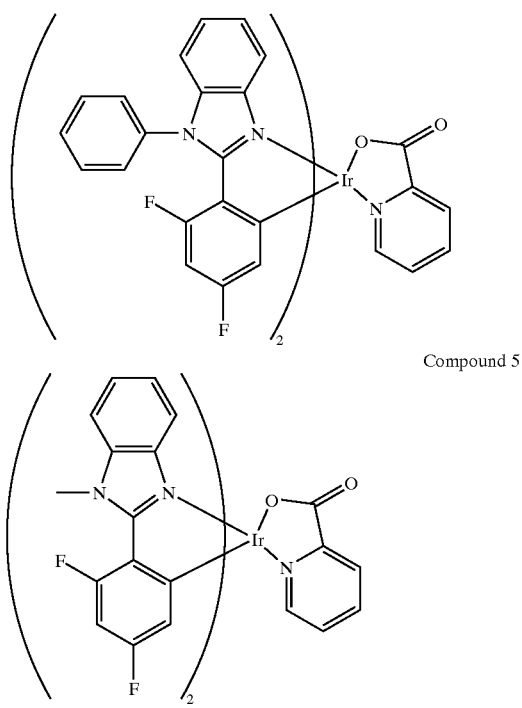

Compound 5

Example 1

Synthesis of iridium(III)bis[1,2-diphenyl-1H-benzoimidazole] (picolinate) (Compound 1)

The synthesis pathway is shown below.

Step 1: 40 ml of N-phenyl-1,2-phenylenediamine (7.36 g, 40 mmol) was charged in a 250 ml round bottle, 10 ml of triethylamine was then added, and the mixture was cooled to 0° C. Benzoyl chloride (5.6 g, 40 mmol) was dissolved in 40 ml of dichloromethane and then slowly added to the 250 ml round bottle. The reaction was conducted under a nitrogen atmosphere for 6 hours. After the reaction was complete, ether was added to form precipitation. The solid product was collected by filtration, washed with ether several times, and heated under reduced pressure to form 1,2-diphenyl-1H-benzoimidazole (yield=7.56 g, 70%).

Step 2: 1,2-diphenyl-1H-benzoimidazole (6.75 g, 25 mmol) and iridium(III) chloride trihydrate (4.2 g, 12 mmol) were mixed and then a mixed solution containing 60 ml of ethyoxyethanol and 20 ml of water was added. The mixture was heated to reflux under a nitrogen atmosphere for 12 hours and then cooled to form yellow precipitate. The precipitate was washed with D.I. water and hexane several times to give iridium dichloro-bridged dimer (7.35 g, 4.8 mmol).

Step 3: The iridium dichloro-bridged dimer (7.35 g, 4.8 mmol) and picolinic acid (1.23 g, 10 mmol) were added to 60 ml of ethyoxyethanol and then sodium carbonate (1.06 g, 10 mmol) was added. The mixture was heated to reflux under a nitrogen atmosphere for 16 hours. After cooled to room temperature, the solid was collected by filtration, and then washed with D.I. water several times, followed by several rinses with ethanol followed by hexane to give Iridium(III)bis[1,2-Diphenyl-1H-benzoimidazole] (picolinate) (5.7 g, 6.7 mmol) (compound 1) The final product was purified by vacuum sublimation.

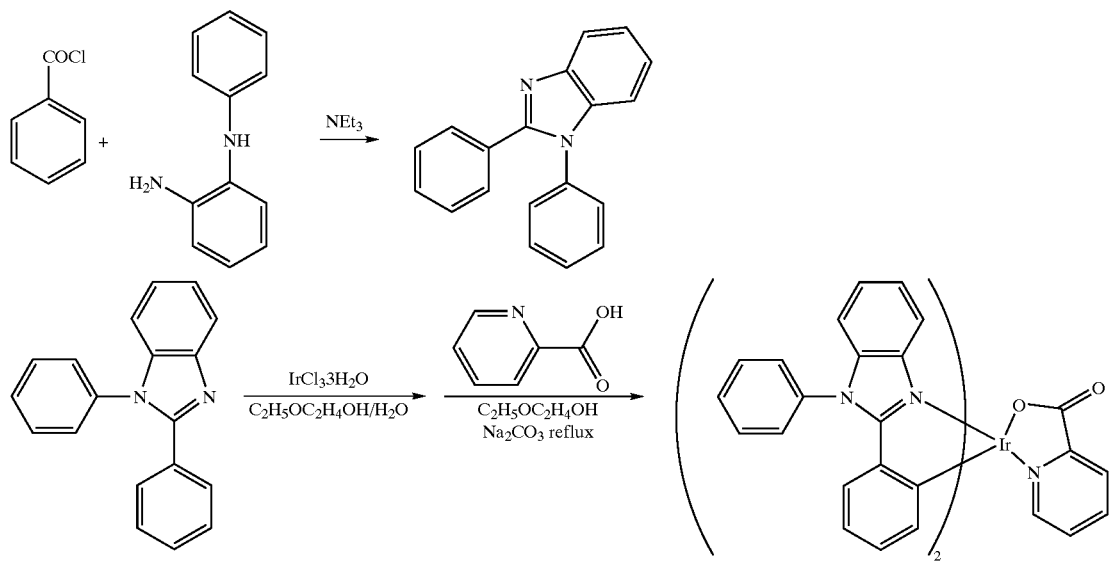

Example 2

Synthesis of iridium(III)bis[2-(4-Fluorophenyl)-1-phenyl-1H-benzoimidazole](picolinate) (Compound 2)

Step 1: N-phenyl-1,2-phenylenediamine (1.84 g, 10 mmol) and 30 ml of dichloromethane were charged in a 250 ml round bottle, 3 ml of triethylamine was then added, and the mixture was cooled to 0° C. 4-Fluoro-benzoyl chloride (1.58 g, 10 mmol) was dissolved in 30 ml of dichloromethane and then slowly added to the 250 ml round bottle. The reaction was conducted under a nitrogen atmosphere for 6 hours. After the reaction was complete, ether was added to form precipitation. The solid product was collected by filtration, washed with ether several times, and heated under reduced pressure to form 2-(4-fluoro-phenyl)-1-phenyl-1H-benzoimidazole (yield= 2.3 g, 80%).

Step 2: 2-(4-fluoro-phenyl)-1-phenyl-1H-benzoimidazole (2.3 g, 8 mmol) and iridium(III) chloride trihydrate (1.41 g, 4 mmol) were mixed and then a mixed solution containing 30 ml of ethyoxyethanol and 10 ml of water was added. The mixture was heated to reflux under a nitrogen atmosphere for 12 hours and then cooled to form yellow precipitate. The precipitate was washed with D.I. water and hexane several times to give iridium dichloro-bridged dimer (3.2 g, 2 mmol).

Step 3: The iridium dichloro-bridged dimer (3.2 g, 2 mmol) and picolinic acid (0.49 g, 4 mmol) were added to 30 ml of ethyoxyethanol and then sodium carbonate (0.53 g, 5 mmol) was added. The mixture was heated to reflux under a nitrogen atmosphere for 16 hours. After cooled to room temperature, the solid was collected by filtration, and then washed with D.I. water several times, followed by several rinses with ethanol followed by hexane to give iridium(III)bis[2-(4-fluoro-phenyl)-1-phenyl-1H-benzoimidazole] (picolinate) (3.1 g, 3.5 mmol) (Compound 2). The final product was purified by vacuum sublimation.

Example 3

Synthesis of iridium(III)bis[2-(2-Fluorophenyl)-1-phenyl-1H-benzoimidazole](picolinate) (Compound 3)

Step 1: N-phenyl-1,2-phenylenediamine (3.68 g, 20 mmol) and 40 ml of dichloromethane were charged in a 250 ml round bottle, 5 ml of triethylamine was then added, and the mixture was cooled to 0° C. 2-Fluoro-benzoyl chloride (3.16 g, 20 mmol) was dissolved in 40 ml of dichloromethane and then slowly added to the 250 ml round bottle. The reaction was conducted under a nitrogen atmosphere for 6 hours. After the reaction was complete, ether was added to form precipitation. The solid product was collected by filtration, washed with ether several times, and heated under reduced pressure to form 2-(2-fluoro-phenyl)-1-phenyl-1H-benzoimidazole (yield=4.32 g, 75%).

Step 2: 2-(2-fluoro-phenyl)-1-phenyl-1H-benzoimidazole (4.03 g, 14 mmol) and iridium(III) chloride trihydrate (2.47 g, 7 mmol) were mixed and then a mixed solution containing 30 ml of ethyoxyethanol and 10 ml of water was added. The mixture was heated to reflux under a nitrogen atmosphere for 12 hours and then cooled to form yellow precipitate. The precipitate was washed with D.I. water and hexane several times to give iridium dichloro-bridged dimer (4.8 g, 3 mmol).

Step 3: The iridium dichloro-bridged dimer (4.8 g, 3 mmol) and picolinic acid (0.75 g, 6 mmol) were added to 30 ml of ethyoxyethanol and then sodium carbonate (0.79 g, 7.5 mmol) was added. The mixture was heated to reflux under a nitrogen atmosphere for 16 hours. After cooled to room temperature, the solid was collected by filtration, and then washed with D.I. water several times, followed by several rinses with ethanol followed by hexane to give iridium(III)bis[2-(2-fluoro-phenyl)-1-phenyl- 1H-benzoimidazole](picolinate) (4.4 g, 5 mmol) (Compound 3). The final product was purified by vacuum sublimation.

Example 4

Synthesis of iridium(III)bis[2-(2,4-difluorophenyl)-1-phenyl-1H-benzoimidazole](picolinate) (Compound 4)

Step 1: N-phenyl-1,2-phenylenediamine (1.84 g, 10 mmol) and 40 ml of dichloromethane were charged in a 250 ml round bottle, 3 ml of triethylamine was then added, and the mixture was cooled to 0° C. 2,4-Difluoro-benzoyl chloride (1.94 g, 11 mmol) was dissolved in 40 ml of dichloromethane and then slowly added to the 250 ml round bottle. The reaction was conducted under a nitrogen atmosphere for 6 hours. After the reaction was complete, ether was added to form precipitation. The solid product was collected by filtration, washed with ether several times, and heated under reduced pressure to form 2-(2,4-difluoro-phenyl)-1-phenyl-1H-benzoimidazole (yield=1.83 g, 60%).

Step 2: 2-(2,4-difluoro-phenyl)-1-phenyl-1H-benzoimidazole (1.83 g, 6 mmol) and iridium(III) chloride trihydrate (1.1 g, 3 mmol) were mixed and then a mixed solution containing 30 ml of ethyoxyethanol and 10 ml of water was added. The mixture was heated to reflux under a nitrogen atmosphere for 12 hours and then cooled to form yellow precipitate. The precipitate was washed with D.I. water and hexane several times to give iridium dichloro-bridged dimer (2.01 g, 1.2 mmol).

Step 3: The iridium dichloro-bridged dimer (2.01 g, 1.2 mmol) and picolinic acid (0.31 g, 2.5 mmol) were added to 30 ml of ethyoxyethanol and then sodium carbonate (0.28 g, 2.5 mmol) was added. The mixture was heated to reflux under a nitrogen atmosphere for 16 hours. After cooled to room temperature, the solid was collected by filtration, and then washed with D.I. water several times, followed by several rinses with ethanol followed by hexane to give iridium(III)bis[2-(2,4-difluoro-phenyl)-1-phenyl-1H-benzoimidazole](picolinate) (1.85 g, 2 mmol) (Compound 4). The final product was purified by vacuum sublimation.

Example 5

Synthesis of iridium(III)bis[ 2-(2,4-difluoro-phenyl)-1-methyl-1H-benzoimidazole] (picolinate) (Compound 5)

Step 1: N-methyl-benzene 1,2-diamine (1.22 g, 10 mmol) and 40 ml of dichloromethane were charged in a 250 ml round bottle, 3 ml of triethylamine was then added, and the mixture was cooled to 0° C. 2,4-Difluoro-benzoyl chloride (1.77 g, 10 mmol) was dissolved in 40 ml of dichloromethane and then slowly added to the 250 ml round bottle. The reaction was conducted under a nitrogen atmosphere for 6 hours. After the reaction was complete, ether was added to form precipitation. The solid product was collected by filtration, washed with ether several times, and heated under reduced pressure to form 2-(2,4-difluoro-phenyl)-1-methyl-1H-benzoimidazole (yield=1.97 g, 81%).

Step 2: 2-(2,4-difluoro-phenyl)-1-methyl-1H-benzoimidazole (1.97 g, 8 mmol) and iridium(III) chloride trihydrate (1.41 g, 4 mmol) were mixed and then a mixed solution containing 30 ml of ethyoxyethanol and 10 ml of water was added. The mixture was heated to reflux under a nitrogen atmosphere for 12 hours and then cooled to form yellow precipitate. The precipitate was washed with D.I. water and hexane several times to give iridium dichloro-bridged dimer (1.5 g, 1.2 mmol).

Step 3: The iridium dichloro-bridged dimer (1.5 g, 1.2 mmol) and picolinic acid (0.31 g, 2.5 mmol) were added to 30 ml of ethyoxyethanol and then sodium carbonate (0.28 g, 2.5 mmol) was added. The mixture was heated to reflux under a nitrogen atmosphere for 16 hours. After cooled to room temperature, the solid was collected by filtration, and then washed with D.I. water several times, followed by several rinses with ethanol followed by hexane to give iridium(III) bis[2-(2,4-difluoro-phenyl)-1-methyl-1H-benzoimidazole] (picolinate) (1.85 g, 2 mmol) (Compound 5). The final product was purified by vacuum sublimation.

The fluorescent spectra of compounds 1 to 5 at various wavelengths are together shown in FIG. 1. For compound 1, there is no substituent on the benzene ring that connects imidazole ring and Ir. It can be seen from the spectrum of compound 1 that the light emission maximum wavelengths are 506 nm and 529 nm. When the benzene ring is substituted with F (an electron-withdrawing group) in the para position as compound 2, there is a blue shift to 491 nm. When the benzene ring is substituted with F in the meta position (compound 3), the light emission wavelength is 505 nm, almost the same as in the para position.

When the benzene ring that connects imidazole ring and Ir is substituted with two F atoms (compound 4), the light emission wavelength blue shifts to 489 nm.

In addition, when the benzene ring (phenyl) on the N atom of imidazole in compound 4 is replaced with methyl (a stronger electron-donating group than phenyl)

(compound 5), a greater blue shift occurs (shifting to 480 nm).

The foregoing description of the preferred embodiments of this invention has been presented for purposes of illustration and description. Obvious modifications or variations are possible in light of the above teaching. The embodiments chosen and described provide an excellent illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. An organometallic complex having formula (I)

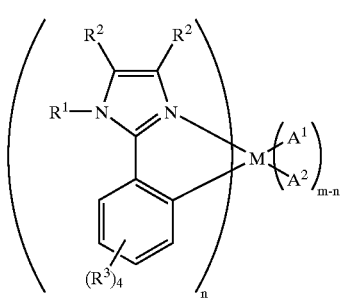

(I)

wherein

M is a transition metal;

each $A^1$ and $A^2$ is independently a monodentate ligand, or $A^1$ and $A^2$ are covalently joined together to form a bidentate ligand;

$R^1$ is H, $C_{1-18}$ alkyl, $C_{1-18}$ alkoxy, $C_{3-18}$ heteroalkyl, $C_{3-20}$ aryl, $C_{3-20}$ heteroaryl, or $C_{3-20}$ cycloalkyl;

$R^2$ is the same or different and is $C_{1-18}$ alkyl, $C_{1-18}$ alkoxy, $C_{3-18}$ heteroalkyl, $C_{3-20}$ aryl, $C_{3-20}$ heteroaryl, or $C_{3-20}$ cycloalkyl;

$R^3$ is the same or different and is H, CN, tricyanovinyl, halogen, $CX_3$, $C_{1-18}$ alkyl, $C_{1-18}$ alkoxy, $C_{3-18}$ heteroalkyl, $C_{3-20}$ aryl, $C_{3-20}$ heteroaryl, or $C_{3-20}$ cycloalkyl, wherein X is halogen;

m is the charge of M;

n is 1, 2, or 3.

2. The organometallic complex as claimed in claim 1, wherein M is Ir, Pt, Os, Re, Ru, or Rh.

3. The organometallic complex as claimed in claim 1, wherein $A^1$ and $A^2$ are covalently joined together to form a bidentate ligand.

4. The organometallic complex as claimed in claim 1, wherein $R^1$ is an electron-donating group.

5. The organometallic complex as claimed in claim 1, wherein $R^1$ is $C_{1-18}$ alkyl, $C_{1-18}$ alkoxy, $C_{3-18}$ heteroalkyl, $C_{3-20}$ aryl, or $C_{3-20}$ heteroaryl.

6. The organometallic complex as claimed in claim 1, wherein $R^3$ is an electron-withdrawing group.

7. The organometallic complex as claimed in claim 1, wherein $R^3$ is halogen, CN, tricyanovinyl or $CX_3$, wherein X is halogen.

8. The organometallic complex as claimed in claim 7, wherein $R^3$ is halogen.

9. The organometallic complex as claimed in claim 1, which emits light.

10. The organometallic complex as claimed in claim 9, which emits phosphorescence.

11. The organometallic complex as claimed in claim 10, which emits blue phosphorescence.

12. The organometallic complex as claimed in claim 1, which has a hole transport property.

13. An organic electroluminescent device, comprising a pair of electrodes and a layer of organic light emitting medium disposed between the pair of electrodes, wherein the layer of organic light emitting medium includes an organometallic complex having formula (I)

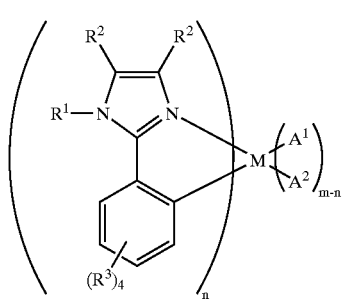

(I)

wherein

M is a transition metal;

each $A^1$ and $A^2$ is independently a monodentate ligand, or $A^1$ and $A^2$ are covalently joined together to form a bidentate ligand;

$R^1$ is H, $C_{1-18}$ alkyl, $C_{1-18}$ alkoxy, $C_{3-20}$ heteroalkyl, $C_{3-20}$ aryl, $C_{3-20}$ heteroaryl, or $C_{3-20}$ cycloalkyl;

$R^2$ is the same or different and is $C_{1-18}$ alkyl, $C_{1-18}$ alkoxy, $C_{3-20}$ heteroalkyl, $C_{3-20}$ aryl, $C_{3-20}$ heteroaryl, or $C_{3-20}$ cycloalkyl;

$R^3$ is the same or different and is H, CN, tricyanovinyl, halogen, $CX_3$, $C_{1-18}$ alkyl, $C_{1-18}$ alkoxy, $C_{3-18}$ heteroalkyl, $C_{3-20}$ aryl, $C_{3-20}$ heteroaryl, or $C_{3-20}$ cycloalkyl, wherein X is halogen;

m is the charge of M;

n is 1, 2, or 3.

14. The organic electroluminescent device as claimed in claim 13, wherein the layer of organic light emitting medium includes a light emitting layer, and the light emitting layer includes an organometallic complex of formula (I).

15. The organic electroluminescent device as claimed in claim 13, wherein the layer of organic light emitting medium includes a light emitting layer and a hole transport layer, and the hole transport layer includes an organometallic complex of formula (I).

16. An organometallic complex, which is selected from the following formulae

Compound 1

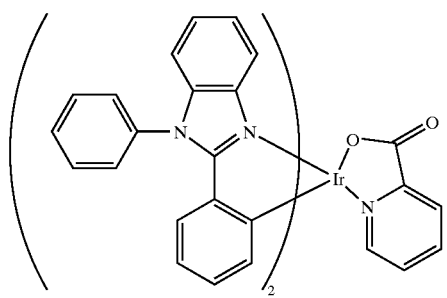

Compound 2

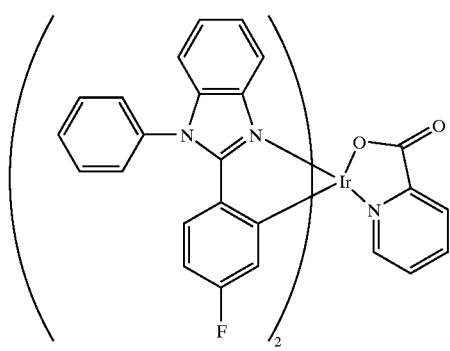

Compound 3

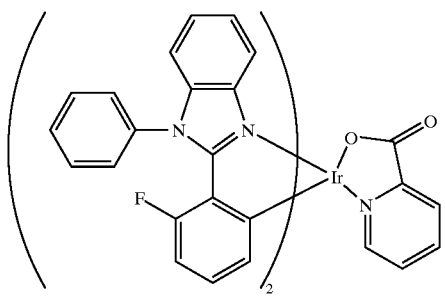

Compound 4

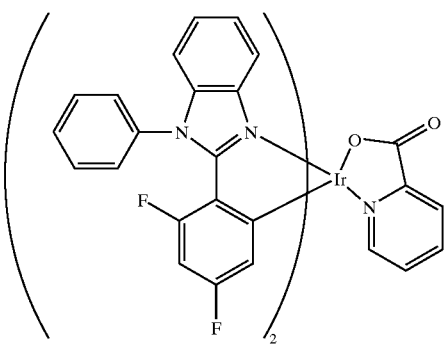

Compound 5

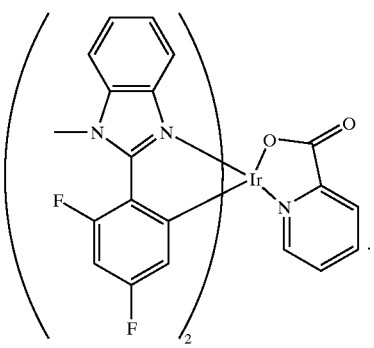

17. An organic electroluminescent device, comprising a pair of electrodes and a layer of organic light emitting medium disposed between the pair of electrodes, wherein the layer of organic light emitting medium includes an organometallic complex, which is selected from the following formulae Compound 1

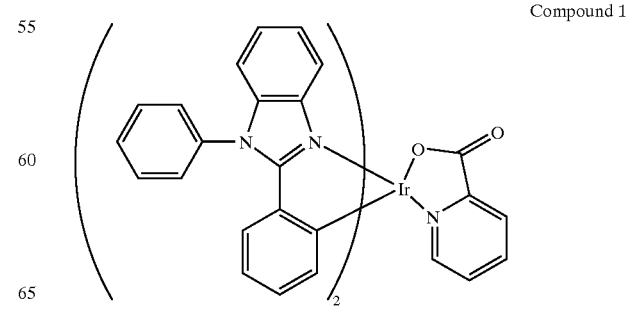

-continued
Compound 2
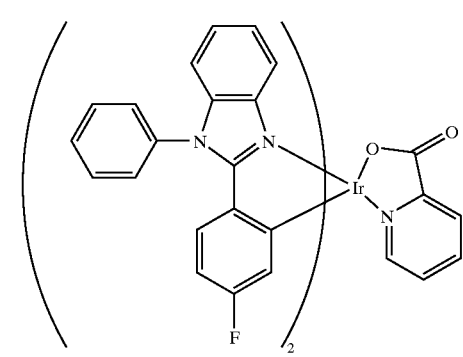
Compound 3
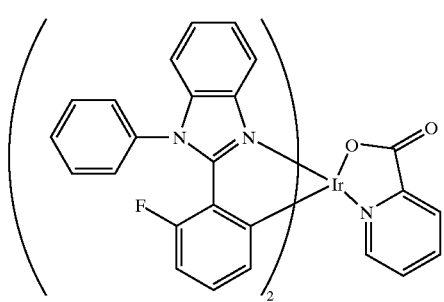
-continued
Compound 4
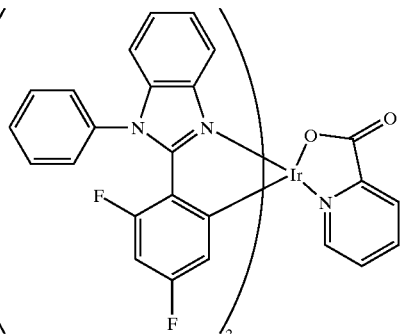
Compound 5
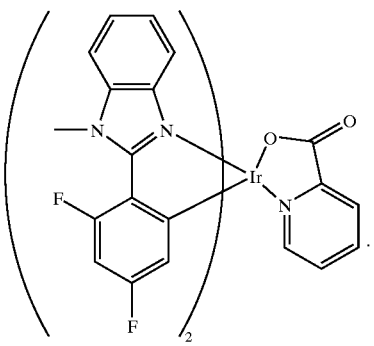
* * * * *